US010456578B2

(12) United States Patent
Karunasiri

(10) Patent No.: US 10,456,578 B2
(45) Date of Patent: Oct. 29, 2019

(54) UTILIZATION OF AN EXTENDED INTER-PULSE INTERVAL IN A MODIFIED CONTINUOUS INTERLEAVED STIMULATION STRATEGY

(71) Applicant: ADVANCED BIONICS AG, Staefa (CH)

(72) Inventor: R. Tissa Karunasiri, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 289 days.

(21) Appl. No.: 15/315,355

(22) PCT Filed: Jun. 4, 2015

(86) PCT No.: PCT/US2015/034183
§ 371 (c)(1),
(2) Date: Nov. 30, 2016

(87) PCT Pub. No.: WO2015/199934
PCT Pub. Date: Dec. 30, 2015

(65) Prior Publication Data
US 2017/0113041 A1   Apr. 27, 2017

Related U.S. Application Data

(60) Provisional application No. 62/016,889, filed on Jun. 25, 2014.

(51) Int. Cl.
*A61N 1/00* (2006.01)
*A61N 1/36* (2006.01)
*A61N 1/05* (2006.01)

(52) U.S. Cl.
CPC ....... *A61N 1/36036* (2017.08); *A61N 1/0541* (2013.01)

(58) Field of Classification Search
CPC ............ A61N 1/36032; A61N 1/36036; A61N 1/0541; A61N 1/36038; A61N 1/36039
See application file for complete search history.

(56) References Cited

U.S. PATENT DOCUMENTS 6,002,966 A   12/1999   Loeb et al.
6,219,580 B1   4/2001   Faltys et al.
(Continued)

OTHER PUBLICATIONS

Wieringen, et al., "Alternative Pulse Shapes in Electrical Hearing", *Hearing Research* 242 (2008), 154-163.
(Continued)

*Primary Examiner* — Mallika D Fairchild
(74) *Attorney, Agent, or Firm* — ALG Intellectual Property, LLC

(57) ABSTRACT

An exemplary sound processor included in a cochlear implant system comprises a control facility that represents a first frequency domain signal to a patient by 1) directing a cochlear implant included in the cochlear implant system to apply, during a first stimulation frame, a first monophasic stimulation pulse representative of a first temporal portion of the first frequency domain signal that corresponds to the first stimulation frame, the first monophasic stimulation pulse having a first polarity, and 2) directing the cochlear implant to apply, during a second stimulation frame that is temporally subsequent to the first stimulation frame, a second monophasic stimulation pulse representative of a second temporal portion of the first frequency domain signal that corresponds to the second stimulation frame, the second monophasic stimulation pulse configured to at least partially charge balance the first monophasic stimulation pulse and having a second polarity opposite the first polarity.

19 Claims, 7 Drawing Sheets

(56) References Cited

U.S. PATENT DOCUMENTS

| | | |
|---|---|---|
| 6,600,955 B1 | 7/2003 | Zierhofer |
| 7,167,754 B1 * | 1/2007 | Peeters .............. A61N 1/36036 607/57 |
| 9,044,610 B2 | 6/2015 | Rosenberg et al. |
| 2005/0222644 A1 | 10/2005 | Killian et al. |

OTHER PUBLICATIONS

Wieringen, et al., "Effects of Waveform Shape on Human Sensitivity to Electrical Stimulation of the Inner Ear", *Hearing Research* 200 (2005), 73-86.

Macherey, et al., "Higher Sensitivity of Human Auditory Nerve Fibers to Positive Electrical Currents", *Journal of the Association for Research in Otolaryngology (JARO)*, 9 (2008), 241-251.

Bonnet, et al., "Speech Recognition with a Cochlear Implant Using Triphasic Charge-balanced Pulses", *Acta Otolaryngol* 2004; 124, 371-375.

International Search Report and Written Opinion received in International Application No. PCT/US15/034183, dated Aug. 17, 2015.

\* cited by examiner

UTILIZATION OF AN EXTENDED INTER-PULSE INTERVAL IN A MODIFIED CONTINUOUS INTERLEAVED STIMULATION STRATEGY

RELATED APPLICATIONS

The present application claims priority to U.S. Provisional Patent Application No. 62/016,889, filed Jun. 25, 2014, the contents of which are hereby incorporated by reference in their entirety.

BACKGROUND INFORMATION

The natural sense of hearing in human beings involves the use of hair cells in the cochlea that convert or transduce acoustic signals into auditory nerve impulses. Hearing loss, which may be due to many different causes, is generally of two types: conductive and sensorineural. Some types of conductive hearing loss occur when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea, which are needed to transduce acoustic signals into auditory nerve impulses. People who suffer from severe to profound sensorineural hearing loss may be unable to derive significant benefit from conventional hearing aid systems, no matter how loud the acoustic stimulus. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous cochlear implant systems—or cochlear prostheses—have been developed. Cochlear implant systems bypass the hair cells in the cochlea by presenting electrical stimulation directly to the auditory nerve fibers by way of an array of electrodes implanted within the cochlea. Direct stimulation of the auditory nerve fibers leads to the perception of sound in the brain and at least partial restoration of hearing function.

Typically, cochlear implant systems utilize either a Continuous Interleaved Stimulation ("CIS") strategy or a Simultaneous Analog Stimulation ("SAS") strategy to represent an audio signal to a patient. In SAS, all of the electrodes in an electrode array are stimulated simultaneously during a stimulation frame. Because of this, SAS requires a relatively high amount of power. CIS requires less energy and hence is more power efficient than SAS, but relies on a bi-phasic pulse in which a second pulse is provided right after a first pulse during a stimulation frame to retrieve or balance the charge delivered to the electrode by the first pulse. The second pulse, which does not contribute to loudness growth of the first pulse, results in wasted energy.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
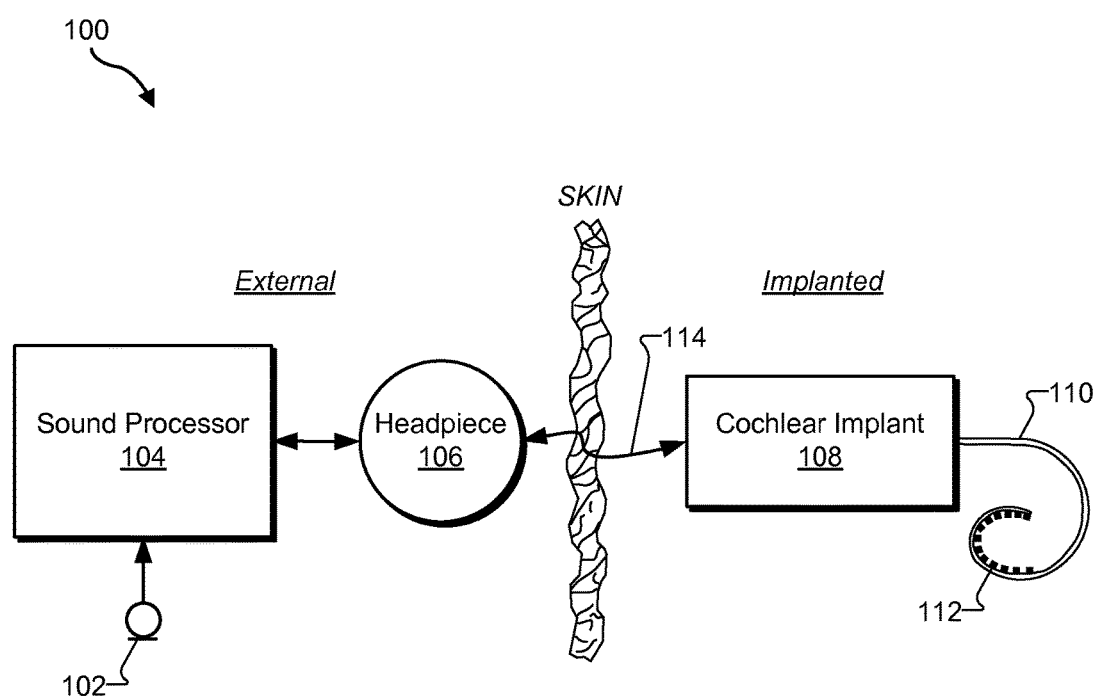
FIG. 1 illustrates an exemplary cochlear implant system according to principles described herein.

Systems and methods that facilitate utilization of an extended inter-pulse interval in a modified CIS strategy are described herein. As will be described in more detail below, a sound processor included in a cochlear implant system associated with a patient may receive an audio signal presented to the patient, divide the audio signal into a plurality of analysis channels each containing a frequency domain signal representative of a distinct frequency portion of the audio signal, and represent each frequency domain signal to the patient in accordance with a modified CIS strategy that utilizes an extended inter-pulse interval.

To illustrate, the plurality of analysis channels may include a first analysis channel corresponding to a first electrode and that contains a first frequency domain signal. To represent the first frequency domain signal to the patient, the sound processor may direct a cochlear implant included in the cochlear implant system to apply, during a first stimulation frame, a first monophasic stimulation pulse representative of a first temporal portion of the first frequency domain signal that corresponds to the first stimulation frame. The first monophasic stimulation pulse may have a first polarity (e.g., a positive polarity). The sound processor may then direct the cochlear implant to apply, during a second stimulation frame that is temporally subsequent to the first stimulation frame, a second monophasic stimulation pulse representative of a second temporal portion of the first frequency domain signal that corresponds to the second stimulation frame. The second monophasic stimulation pulse may be configured to at least partially charge balance the first monophasic stimulation pulse and may have a second polarity (e.g., a negative polarity) opposite the first polarity.

As will be described in more detail below, an extended inter-pulse interval separates the first and second monophasic stimulation pulses. During the extended inter-pulse interval, the sound processor may direct the cochlear implant to apply charge balancing stimulation to the first electrode. The charge balancing stimulation may have a nominal amplitude that is not perceptible by the patient and may ensure that the first and second monophasic stimulation pulses are fully charge balanced one with another. Additional pairs of charge balancing monophasic pulses separated by extended inter-pulse intervals may similarly be applied to the first electrode during subsequent stimulation frames in order to represent the first frequency domain signal to the patient.

By utilizing the second stimulation pulse to represent the second temporal portion of the first frequency domain signal and to at least partially charge balance the first stimulation pulse, the systems and methods described herein may advantageously allow for a stimulation strategy that utilizes monophasic stimulation pulses (as opposed to biphasic stimulation pulses as conventionally applied in accordance with CIS strategies). In this manner, the systems and methods described herein may conserve power and improve battery life for the cochlear implant system. In addition, by directing, for example, the cochlear implant to apply a monophasic stimulation pulse instead of a biphasic stimulation pulse during a stimulation frame in order to represent a temporal portion of a frequency domain signal that corresponds to the stimulation frame, it may be possible to increase the width of the monophasic stimulation pulse without reducing the overall stimulation frame rate. This may advantageously result in the cochlear implant operating at a lower voltage and thereby achieving lower power consumption. Other benefits of the systems and methods described herein will be made apparent herein.

FIG. 1 illustrates an exemplary cochlear implant system 100. As shown, cochlear implant system 100 may include various components configured to be located external to a patient including, but not limited to, a microphone 102, a sound processor 104, and a headpiece 106. Cochlear implant system 100 may further include various components configured to be implanted within the patient including, but not limited to, a cochlear implant 108 and a lead 110 (also referred to as an electrode array) with a plurality of electrodes 112 disposed thereon. As will be described in more detail below, additional or alternative components may be included within cochlear implant system 100 as may serve a particular implementation. The components shown in FIG. 1 will now be described in more detail.

Microphone 102 may be configured to detect audio signals presented to the patient. Microphone 102 may be implemented in any suitable manner. For example, microphone 102 may include a microphone that is configured to be placed within the concha of the ear near the entrance to the ear canal, such as a T-MIC™ microphone from Advanced Bionics. Such a microphone may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 (i.e., one or more components included within sound processor 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may include or be implemented by a behind-the-ear ("BTE") unit, a body worn device, and/or any other sound processing unit as may serve a particular implementation. For example, sound processor 104 may be implemented by an electro-acoustic stimulation ("EAS") sound processor included in an EAS system configured to provide electrical and acoustic stimulation to a patient.

In some examples, sound processor 104 may wirelessly transmit stimulation parameters (e.g., in the form of data words included in a forward telemetry sequence) and/or RF power signals to cochlear implant 108 by way of a wireless communication link 114 between headpiece 106 and cochlear implant 108. It will be understood that communication link 114 may include a bi-directional communication link and/or one or more dedicated uni-directional communication links.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the patient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or RF power signals may be wirelessly transmitted between sound processor 104 and cochlear implant 108 via a communication link 114 (which may include a bi-directional communication link and/or one or more dedicated uni-directional communication links as may serve a particular implementation).

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of active implant or auditory prosthesis that may be implanted within a patient and configured to apply stimulation to one or more stimulation sites located along an auditory pathway of a patient.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites within the patient via one or more electrodes 112 disposed along lead 110 (e.g., by way of one or more stimulation channels formed by electrodes 112). In some examples, cochlear implant 108 may include a plurality of independent current sources each associated with a channel defined by one or more of electrodes 112. In this manner, different stimulation current levels may be applied to multiple stimulation sites simultaneously (also referred to as "concurrently") or sequentially by way of multiple electrodes 112.

Figure 2:
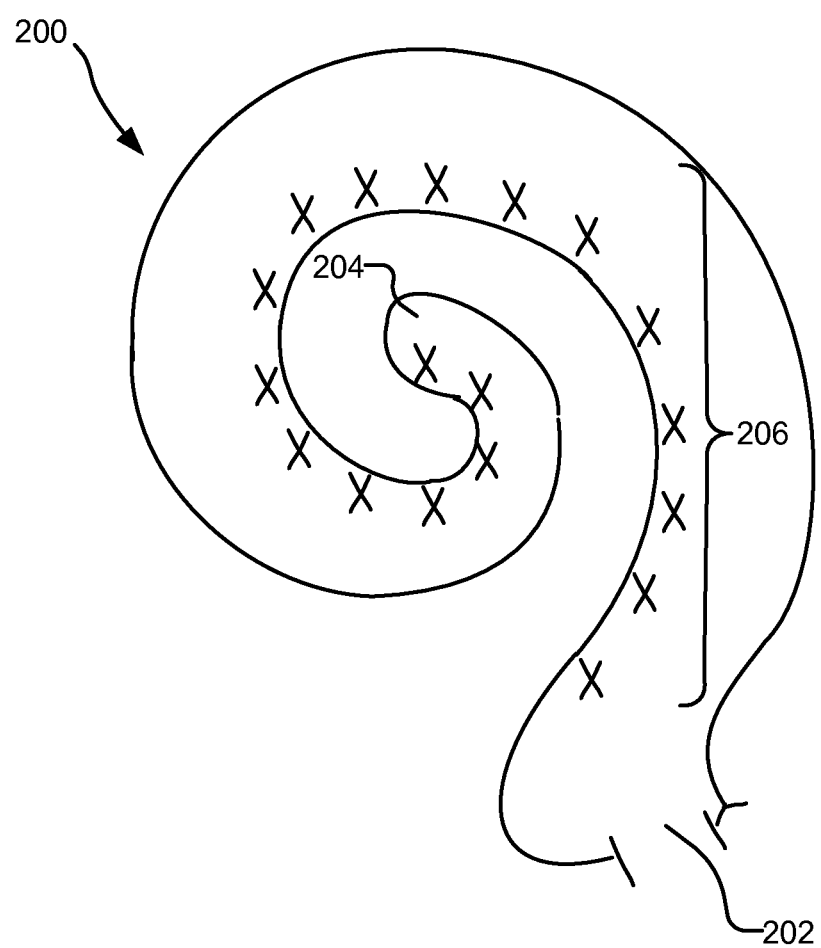
FIG. 2 illustrates a schematic structure of the human cochlea.

FIG. 2 illustrates a schematic structure of the human cochlea 200 into which lead 110 may be inserted. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner.

Relatively low frequencies are encoded at or near the apex 204 of the cochlea 200 (referred to as an "apical region") while relatively high frequencies are encoded at or near the base 202 (referred to as a "basal region"). Hence, each location along the length of the cochlea 200 corresponds to a different perceived frequency. Cochlear implant system 100 may therefore be configured to apply electrical stimulation to different locations within the cochlea 200 (e.g., different locations along the auditory nerve tissue 206) to provide a sensation of hearing.

Figure 3:
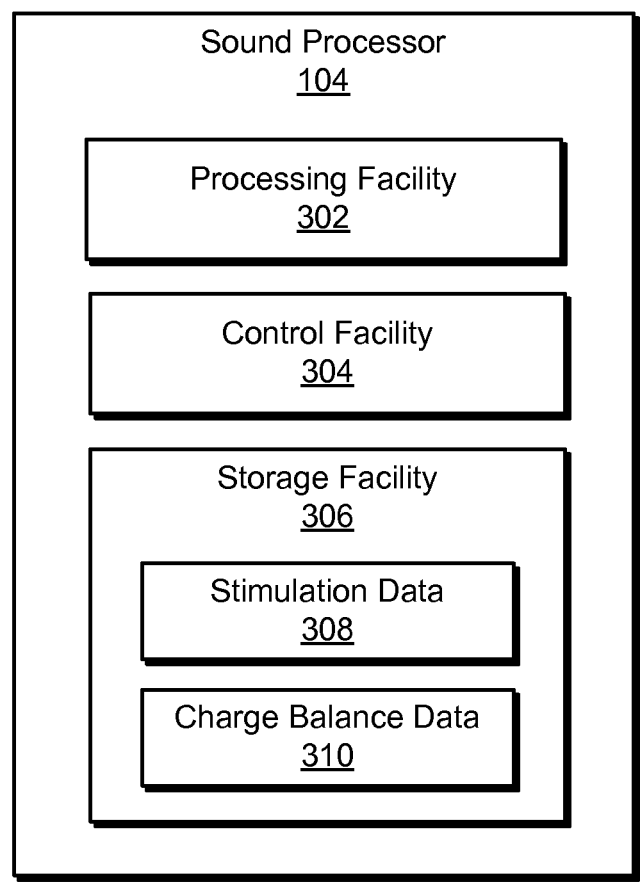
FIG. 3 illustrates exemplary components of a sound processor according to principles described herein.

FIG. 3 illustrates exemplary components of sound processor 104. It will be recognized that the components shown in FIG. 3 are merely representative of the many different components that may be included in sound processor 104 and that sound processor 104 may include additional or alternative components as may serve a particular implementation.

As shown in FIG. 3, sound processor 104 may include a processing facility 302, a control facility 304, and a storage facility 306, which may be in communication with one another using any suitable communication technologies. Storage facility 306 may be configured to maintain stimulation data 308 generated and/or used by processing facility 302 and/or control facility 304, and charge balance data 310 measured and/or used by control facility 304. Storage facility 306 may maintain additional or alternative data as may serve a particular implementation. One or more of facilities 302-306 may include a computing device or processor configured to perform one or more of the functions described herein. Processing facility 302 and control facility 304 will now be described in more detail.

Processing facility 302 may be configured to receive and process an audio signal presented to a cochlear implant patient (e.g., an audio signal detected by microphone 102, an audio signal input by way of an auxiliary audio input port, etc.). For example, processing facility 302 may perform one or more pre-processing operations, spectral analysis operations, noise reduction operations, mapping operations, and/or any other types of signal processing operations on a detected audio signal as may serve a particular application.

In certain examples, processing facility 302 may be configured to divide the audio signal into a plurality of analysis channels each containing a frequency domain signal representative of a distinct frequency portion of the audio signal. For example, processing facility 302 may include a plurality of band-pass filters configured to divide the audio signal into a plurality of frequency channels or bands. Additionally or alternatively, processing facility 302 may be configured to convert the audio signal from a time domain into a frequency domain and then divide the resulting frequency bins into the plurality of analysis channels. To this end, processing facility 302 may include one or more components configured to apply a Discrete Fourier Transform (e.g., a Fast Fourier Transform ("FFT")) to the audio signal.

Processing facility 302 may be configured to divide the audio signal into any number of analysis channels as may serve a particular application. In some examples, the total number of analysis channels is set to be less than or equal to a total number of stimulation channels through which electrical stimulation representative of the audio signal is applied to a cochlear implant patient. In some examples, each analysis channel may correspond to one electrode included in an electrode array implanted within the cochlear implant patient.

The frequency domain signals included in the analysis channels provided by processing system 302 may be represented to the patient utilizing any suitable stimulation strategy. With a conventional CIS strategy, a balanced biphasic stimulation pulse is provided to each electrode in a sequential manner through the electrode array during a single stimulation frame. Each balanced biphasic stimulation pulse may include, for example, a first positive stimulation pulse (or phase) followed immediately by a second negative stimulation pulse (or phase) of equal amplitude. This stimulation sequence is repeated during subsequent stimulation frames at any suitable frequency (e.g., 400 Hz). However, as mentioned, utilizing a biphasic stimulation pulse results in wasted energy because the second phase of the biphasic stimulation pulse does not contribute to loudness growth. Rather, the main purpose of the second phase is to charge balance the first phase. In contrast to a conventional CIS strategy, the systems and methods described herein utilize monophasic stimulation pulses during each stimulation frame, thereby reducing energy consumption and improving battery life.

To this end, after processing facility 302 divides the audio signal into the plurality of analysis channels each containing a frequency domain signal representative of a distinct frequency portion of the audio signal, control facility 304 may represent each frequency portion of the audio signal to the patient in accordance with a modified CIS strategy that includes extended inter-pulse intervals.

Figure 4:
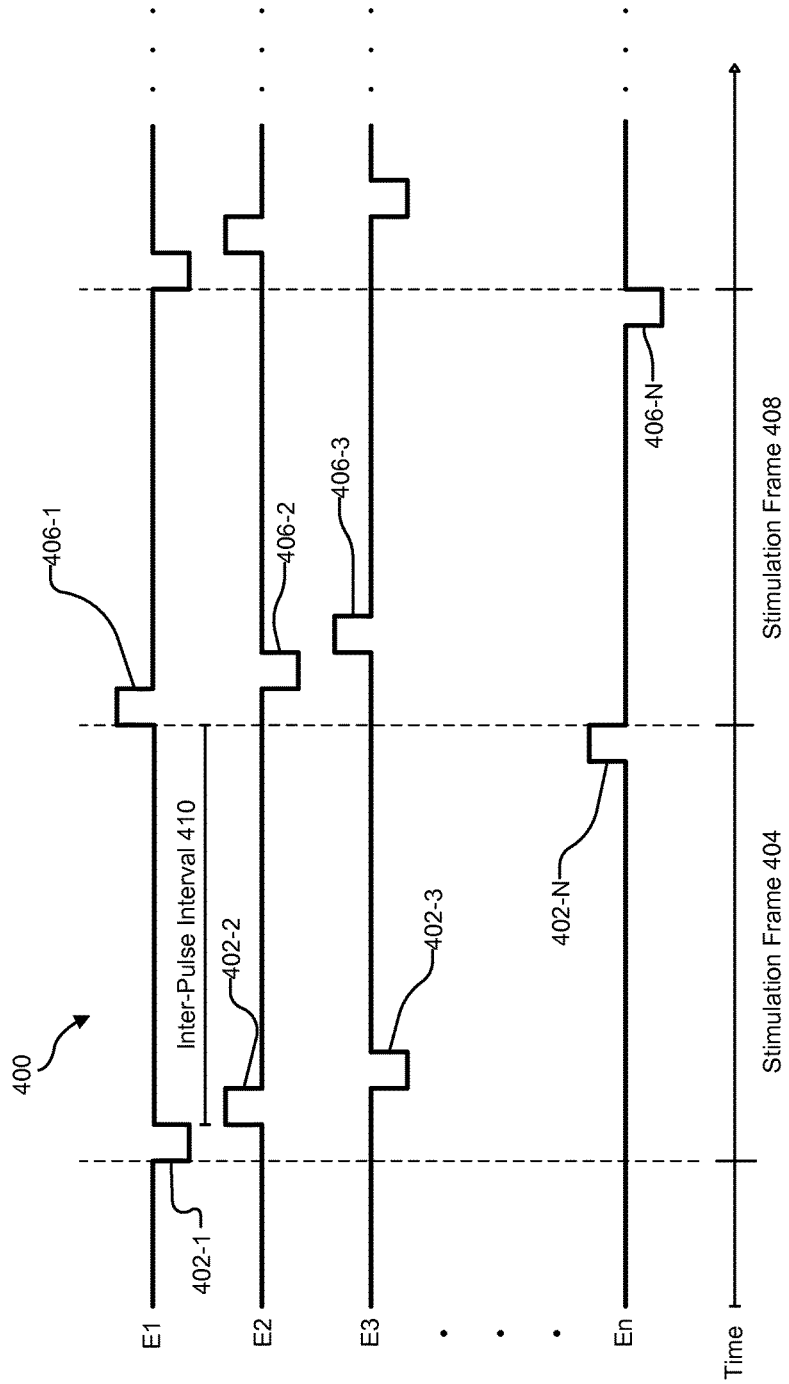
FIGS. 4-5 illustrate exemplary modified CIS stimulation strategies according to principles described herein.

FIG. 4 shows an exemplary modified CIS strategy 400 according to principles described herein. As shown in FIG. 4, control facility 304 may direct, in accordance with the modified CIS strategy 400, a cochlear implant (e.g., cochlear implant 108) to apply monophasic stimulation pulses 402 (e.g., monophasic stimulation pulses 402-1 through 402-N) sequentially to a plurality of electrodes E1 through En during a stimulation frame 404. Electrodes E1-En may be included in electrodes 112, for example, and may include any number of electrodes as may serve a particular implementation.

As used herein, a "monophasic stimulation pulse" refers to a stimulation pulse that has a single phase and represents a portion of an audio signal (i.e., a temporal portion of a frequency domain signal representative of the audio signal) to a patient. The monophasic stimulation pulse may have any suitable polarity (e.g., positive or negative) as may suit a particular implementation.

For example, monophasic stimulation pulse 402-1 is representative of a first temporal portion of a frequency domain signal included in an analysis channel corresponding to electrode E1. Likewise, monophasic stimulation pulse 402-2 is representative of a first temporal portion of a frequency domain signal included in an analysis channel corresponding to electrode E2, etc. Although FIG. 4 shows that each stimulation pulse 402 has the same amplitude, it will be recognized that the amplitude of each stimulation pulse 402 may differ and be set in accordance with an amplitude of each stimulation pulse's corresponding temporal portion.

As used herein, a "stimulation frame" refers to a period of time in which electrical stimulation in the form of a set of monophasic stimulation pulses is applied by a cochlear implant sequentially to electrodes included in an array of electrodes. Only one monophasic stimulation pulse may be applied to any given electrode included in the electrode array in any given stimulation frame. The period of time associated with a stimulation frame may begin when a monophasic stimulation pulse is applied to a first electrode in the electrode array and may end in response to a monophasic stimulation pulse being applied to the last electrode in the electrode array. During electrical stimulation, a plurality of stimulation frames may temporally follow one another. For example, a first stimulation frame, a second stimulation frame, a third stimulation frame, etc. may follow sequentially right after one another as an audio signal is represented to a cochlear implant patient.

In some examples, the monophasic stimulation pulses applied to electrodes E1-En during a given stimulation frame may have alternating polarities. The alternating polarities may serve to provide at least some local charge balancing. For example, as shown in FIG. 4, monophasic stimulation pulse 402-1 applied to electrode E1 has a negative polarity, monophasic stimulation pulse 402-2 applied to electrode E2 has a positive polarity, monophasic stimulation pulse 402-3 applied to electrode E3 has a negative polarity, etc. This alternating polarity pattern may continue sequentially through the entire electrode array to complete stimulation frame 404. It will be recognized that electrodes E1-En may be stimulated in any suitable order as may serve a particular implementation. However, it will be recognized that in some alternative embodiments, the polarities of monophasic stimulation pulses 402 may not alternate. For example, the polarities of monophasic stimulation pulses 402 may all be the same (either negative or positive).

After a monophasic stimulation pulse is applied to the last electrode in the electrode array (e.g., electrode En) during stimulation frame 404, control facility 304 may direct the cochlear implant to apply monophasic stimulation pulses 406 (e.g., monophasic stimulation pulses 406-1 through 406-N) sequentially to electrodes E1-En during a stimulation frame 408. The stimulation sequence in stimulation frame 408 may be similar to the stimulation sequence described above with respect to stimulation frame 404 except that the polarities of the monophasic stimulation pulses 406 applied during stimulation frame 408 may be opposite to those applied during stimulation frame 404.

In the example shown in FIG. 4, stimulation frame 408 is temporally adjacent to and immediately follows stimulation frame 404. However, in certain examples, stimulation frame 408 may be temporally separated from the stimulation frame 404 by one or more intermediate stimulation frames.

Monophasic stimulation pulses 406 are representative of the audio signal during stimulation frame 408. For example, monophasic stimulation pulse 406-1 is representative of a second temporal portion of the frequency domain signal included in the analysis channel that corresponds to electrode E1. Likewise, monophasic stimulation pulse 406-2 is representative of a second temporal portion of the frequency domain signal included in the analysis channel that corresponds to electrode E2, etc. Although FIG. 4 shows that each stimulation pulse 406 has the same amplitude, it will be recognized that the amplitude of each stimulation pulse 406 may differ and be set in accordance with an amplitude of each stimulation pulse's corresponding temporal portion. It will also be recognized that stimulation pulses 406 may have different amplitudes than stimulation pulses 402.

Monophasic stimulation pulses 406 are also configured to at least partially charge balance the monophasic stimulation pulses 402 applied during stimulation frame 404. To this end, each monophasic stimulation pulse 406 may have a polarity opposite that of the polarity of its preceding monophasic stimulation pulse. For example, as shown in FIG. 4, monophasic stimulation pulse 406-1 has a positive polarity and therefore at least partially charge balances the negative stimulation pulse 402-1 that immediately proceeds it on electrode E1. Likewise, monophasic stimulation pulse 406-2 has a negative polarity and therefore at least partially charge balances the positive stimulation pulse 402-2 that immediately proceeds it on electrode E2.

As shown, the duration of the inter-pulse interval between monophasic stimulation pulses applied to the same electrode is extended as compared to the biphasic stimulation pulses provided in a conventional CIS strategy. For example, FIG. 4 shows that an inter-pulse interval 410 between monophasic stimulation pulses 402-1 and 406-1 has a duration that is substantially equal to the first stimulation frame 404 minus a width of the first stimulation pulse 402-1.

In certain examples, an amplitude of a monophasic stimulation pulse applied by the cochlear implant to an electrode in a subsequent stimulation frame may be different (i.e., larger or smaller) than an amplitude of a monophasic stimulation pulse applied to that electrode in a previous stimulation frame. For example, monophasic stimulation pulse 406-1 may have an amplitude that is different than monophasic stimulation pulse 402-1. In these cases, the monophasic stimulation pulses applied to the electrode may not fully charge balance each other.

Accordingly, in certain examples, control facility 304 may be configured to direct the cochlear implant to apply charge balancing stimulation to an electrode during the inter-pulse interval between a pair of monophasic stimulation pulses that are applied to the electrode in order to fully charge balance the monophasic stimulation pulses. For example, with respect to first and second monophasic stimulation pulses applied to a particular electrode (e.g., monophasic stimulation pulses 402-1 and 406-1 applied to electrode E1), control facility 304 may detect a difference in amplitude between the first monophasic stimulation pulse and the second monophasic stimulation pulse, determine, based on the detected difference in amplitude, an amount of charge needed to fully charge balance the first and second monophasic stimulation pulses, and direct the cochlear implant to apply charge balancing stimulation having the determined amount of charge during the inter-pulse interval between the first monophasic stimulation pulse and the second monophasic stimulation pulse. As will be described in more detail below, if the second monophasic stimulation pulse is lower in amplitude than the first monophasic stimulation pulse, the charge balancing stimulation combined with the second monophasic stimulation pulse may fully charge balance the first stimulation pulse. Alternatively, if the first monophasic stimulation pulse is lower in amplitude than the second monophasic stimulation pulse, the charge balancing stimulation combined with the first monophasic stimulation pulse may fully charge balance the second stimulation pulse.

Figure 5:
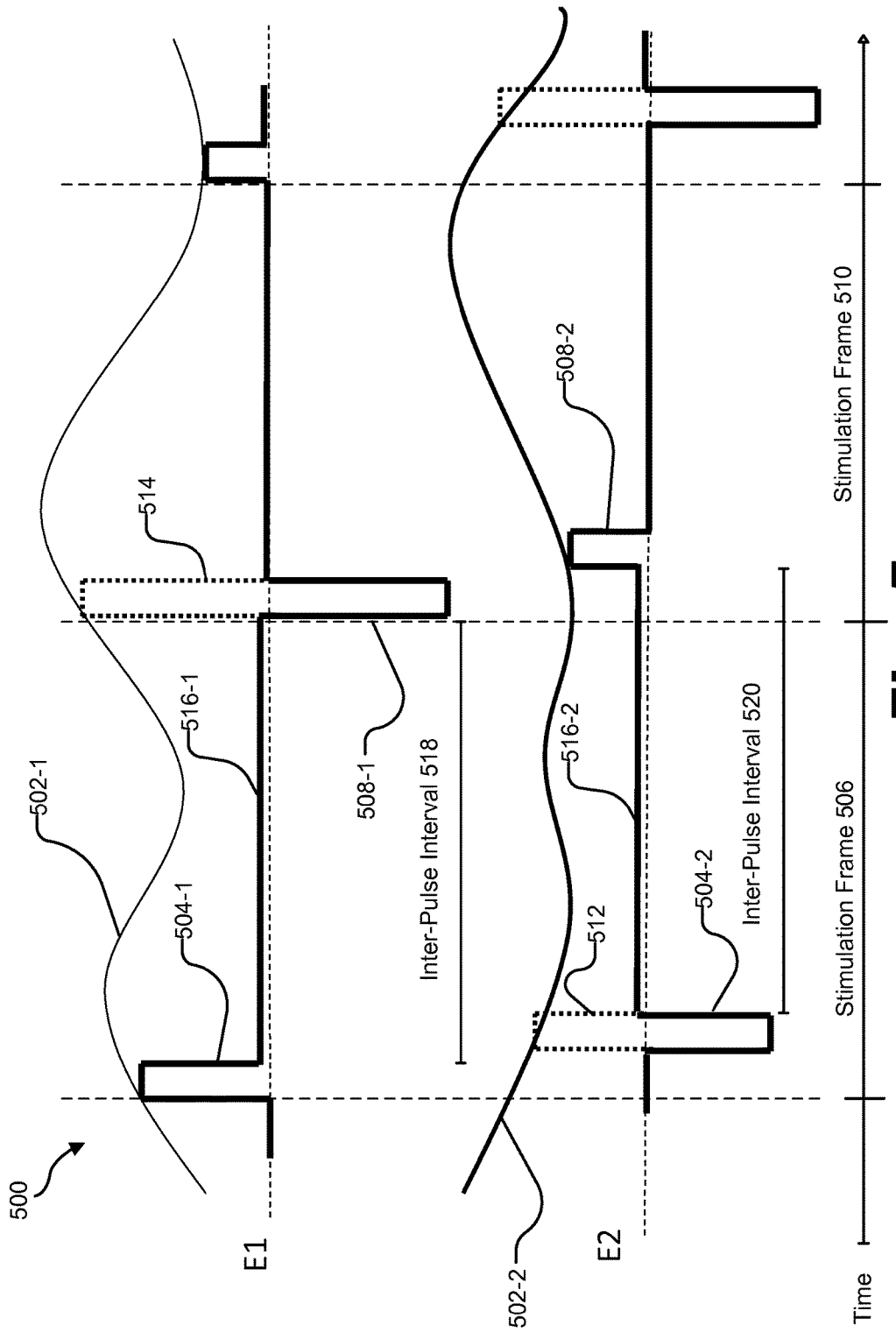

To illustrate, FIG. 5 shows an exemplary modified CIS strategy 500 that utilizes charge balancing stimulation during inter-pulse intervals. Modified CIS strategy 500 may be used to represent frequency domain signals 502 (i.e., frequency domain signals 502-1 and 502-2) in analysis channels corresponding to electrodes E1 and E2 to a patient.

As shown, control facility 304 may direct the cochlear implant to apply monophasic stimulation pulses 504 (e.g., monophasic stimulation pulses 504-1 and 504-2) to electrodes E1 and E2 during stimulation frame 506 in order to represent temporal portions of frequency domain signals 502-1 and 502-2, respectively, that correspond to (i.e., temporally align with) stimulation frame 506. Control facility 304 may also direct the cochlear implant to apply monophasic stimulation pulses 508 (i.e., monophasic stimulation pulses 508-1 and 508-2) to electrodes E1 and E2 during stimulation frame 510 in order to represent temporal portions of frequency domain signals 502-1 and 502-2, respectively, that correspond to (i.e., temporally align with)

stimulation frame 510. As shown, monophasic stimulation pulse 504-1 has a positive polarity and monophasic stimulation pulse 504-2 has a negative polarity. Hence, monophasic stimulation pulse 508-1 applied to electrode E1 during stimulation frame 510 has a negative polarity in order to charge balance monophasic stimulation pulse 504-1 applied to electrode E1 during stimulation frame 506. Likewise, monophasic stimulation pulse 508-1 applied to electrode E2 during stimulation frame 510 has a positive polarity in order to charge balance monophasic stimulation pulse 504-2 applied to electrode E2 during stimulation frame 506.

The amplitudes of each of the monophasic stimulation pulses 504 and 508 are set to correspond to the amplitude (i.e., sound energy) of the frequency domain signals 502 at particular time points at which the monophasic stimulation pulses 504 and 508 are applied. For the negative polarity stimulation pulses 504-2 and 508-1, this is illustrated in FIG. 5 by dotted line portions 512 and 514, respectively. As shown, monophasic stimulation pulse 508-1 is greater in amplitude than monophasic stimulation pulse 504-1. Conversely, monophasic stimulation pulse 508-2 has an amplitude that is less than that of monophasic stimulation pulse 504-2.

To ensure that monophasic stimulation pulses 504-1 and 508-1 are fully charge balanced, control facility 304 may detect a difference in amplitude between monophasic stimulation pulses 504-1 and 508-1, and, based on the detected difference in amplitude, determine an amount of charge needed to fully charge balance monophasic stimulation pulses 504-1 and 508-1.

Control facility 304 may determine the amount of charge needed to fully charge balance monophasic stimulation pulses 504-1 and 508-1 in any suitable manner. For example, the charge included in a given monophasic stimulation pulse may correspond to the area of the monophasic stimulation pulse, which may be derived by multiplying the pulse width and the amplitude of the monophasic stimulation pulse. Accordingly, in certain examples, control facility 304 may utilize data (e.g., stimulation data 308) representative of the pulse width and the amplitude of the monophasic stimulation pulse to determine a charge associated with that monophasic stimulation pulse.

Figure 6:
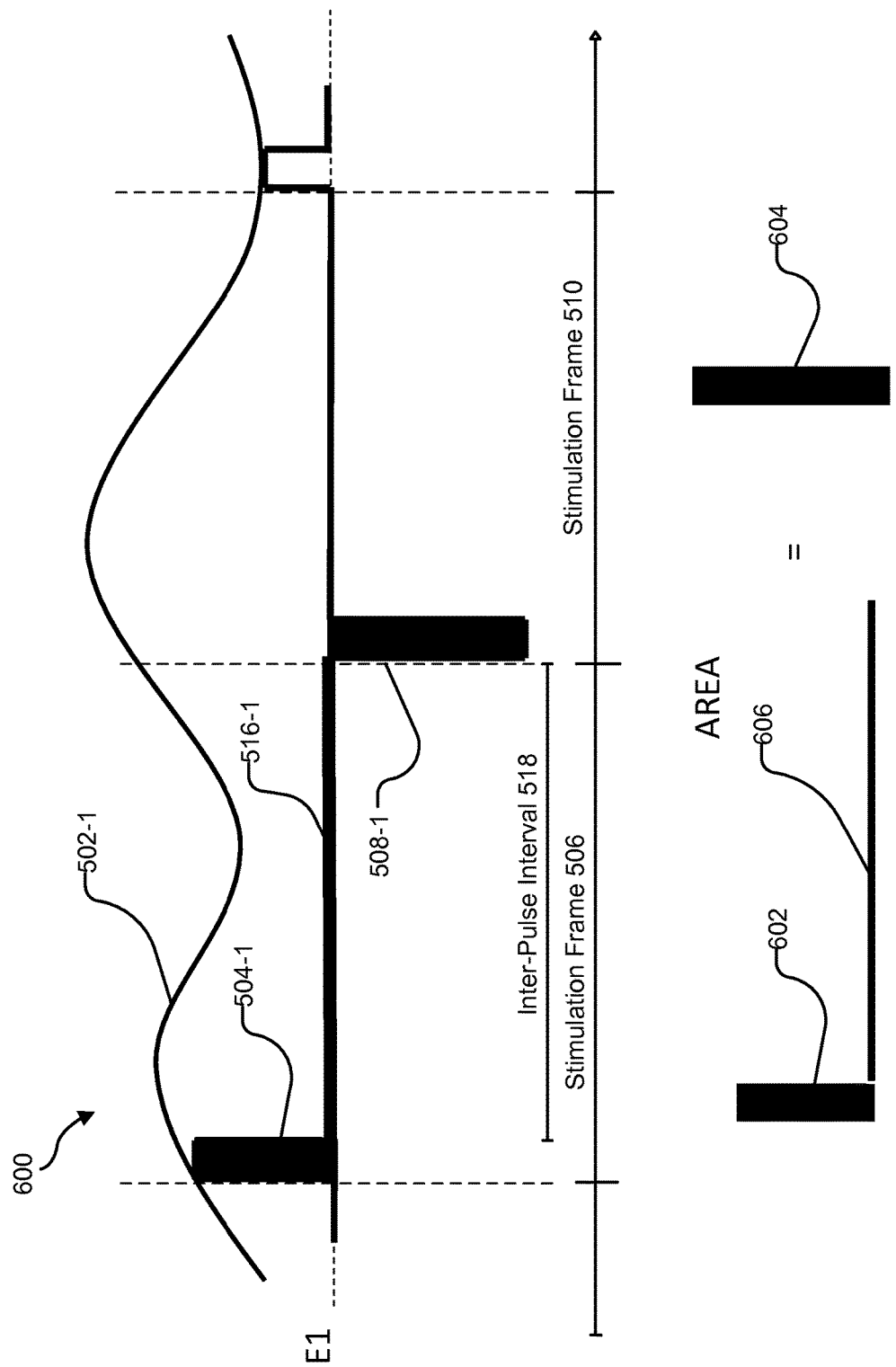
FIG. 6 shows how an amount of charge needed for charge balancing a monophasic stimulation pulse may be determined according to principles described herein.

To illustrate, FIG. 6 illustrates how control facility 304 may determine an amount of charge needed for charge balancing monophasic stimulation pulse 508-1. As mentioned, the amplitude of monophasic stimulation pulse 504-1 is less than the amplitude of monophasic stimulation pulse 508-1. Hence, an area 602 of monophasic stimulation pulse 504-1 is less than an area 604 associated with monophasic stimulation pulse 508-1. To correct for the difference in area, control facility 304 may determine a pulse width and amplitude for charge balancing stimulation 516-1 such that a resulting area 606 associated with charge balancing stimulation 516-1 is substantially equivalent to the difference in area between monophasic stimulation pulse 504-1 and monophasic stimulation pulse 508-1. Accordingly, in the example shown in FIG. 6, the area 602 of monophasic stimulation pulse 504-1 plus the area 606 of charge balancing stimulation 516-1 is substantially equivalent to the area 604 of monophasic stimulation pulse 508-1. In this configuration, monophasic stimulation pulse 508-1 is fully charge balanced.

Returning to FIG. 5, after control facility 304 determines the amount of charge needed to fully charge balance monophasic stimulation pulses 504-1 and 508-1, control facility 304 may direct the cochlear implant to apply charge balancing stimulation having the determined amount of charge during an inter-pulse interval 518 between the monophasic stimulation pulses 504-1 and 508-1. As shown in FIG. 5, inter-pulse interval 518 has a duration substantially equal to a duration of stimulation frame 506 minus a width of monophasic stimulation pulse 504-1.

Control facility 304 may direct the cochlear implant to apply the charge balancing stimulation for any suitable duration and in any suitable manner during inter-pulse interval 518. In certain examples, control facility 304 may direct the cochlear implant to apply the charge balancing stimulation during only a portion (e.g., one half, one third, one quarter, etc.) of inter-pulse interval 518. Alternatively, control facility 304 may direct the cochlear implant to continuously apply the charge balancing stimulation during an entirety of the inter-pulse interval 518. Continuously applying the charge balancing stimulation during the entirety of the inter-pulse interval 518 may facilitate the charge balancing stimulation having a nominal amplitude that is not perceptible by the patient (e.g., the patient does not perceive any sound associated with the charge balancing stimulation).

FIG. 5 illustrates examples of continuously applied charge balancing stimulation. As shown in FIG. 5, charge balancing stimulation 516-1 is applied continuously during inter-pulse interval 518 between monophasic stimulation pulses 504-1 and 508-1. Because the amplitude of monophasic stimulation pulse 508-1 is greater than that of monophasic stimulation pulse 504-1, the polarity of charge balancing stimulation 516-1 is set to be the same as that of monophasic stimulation pulse 504-1 (i.e., positive). In this manner, monophasic stimulation pulse 504-1 and charge balancing stimulation 516-1 may combine to fully charge balance monophasic stimulation pulse 508-1.

Control facility 304 may similarly determine an amount of charge needed to fully charge balance monophasic stimulation pulses 504-2 and 508-2. In the particular example of FIG. 5, control facility 304 may direct the cochlear implant to apply charge balancing stimulation 516-2 having the determined amount of charge during an inter-pulse interval 520 between monophasic stimulation pulses 504-2 and 508-2. Because the amplitude of monophasic stimulation pulse 508-2 is less than that of monophasic stimulation pulse 504-2, the polarity of charge balancing stimulation 516-2 is set to be the same as that of monophasic stimulation pulse 508-2 (i.e., positive). In this manner, monophasic stimulation pulse 508-2 and charge balancing stimulation 516-2 may combine to fully charge balance monophasic stimulation pulse 504-2.

As mentioned, partial charge balancing may occur as a result of oppositely charged monophasic stimulation pulses being applied to adjacent electrodes included in an electrode array. Accordingly, in certain examples, control facility 304 may also take into consideration such a partial charge balancing when determining the amount of charge needed to fully charge balance a monophasic stimulation pulse. To illustrate, in the example shown in FIG. 5, electrode E2 may be adjacent to electrode E1. Because monophasic stimulation pulse 504-2 has a polarity opposite to monophasic stimulation pulse 504-1, monophasic stimulation pulse 504-2 may result in a partial charge balancing of monophasic stimulation pulse 504-1. That is, part of the charge associated with monophasic stimulation pulse 504-1 may be retrieved from electrode E1 as a result of monophasic stimulation pulse 504-2 being applied to electrode E2. In the example shown in FIG. 5, this may increase the difference in amplitude between monophasic stimulation pulse 504-1 and 508-1. To correct for the increased difference in amplitude, control facility 304 may increase an amplitude of charge balancing stimulation 516-1 by an amount commensurate with the amount of charge retrieved from electrode E1 as a result of the partial charge balancing.

The exemplary monophasic stimulation pulses illustrated in FIGS. 5 and 6 are provided for illustrative purposes only. Other monophasic stimulation pulses of different amplitudes and/or pulse widths may be provided in other implementations based on the particular audio signal to be represented to the cochlear implant patient.

Figure 7:
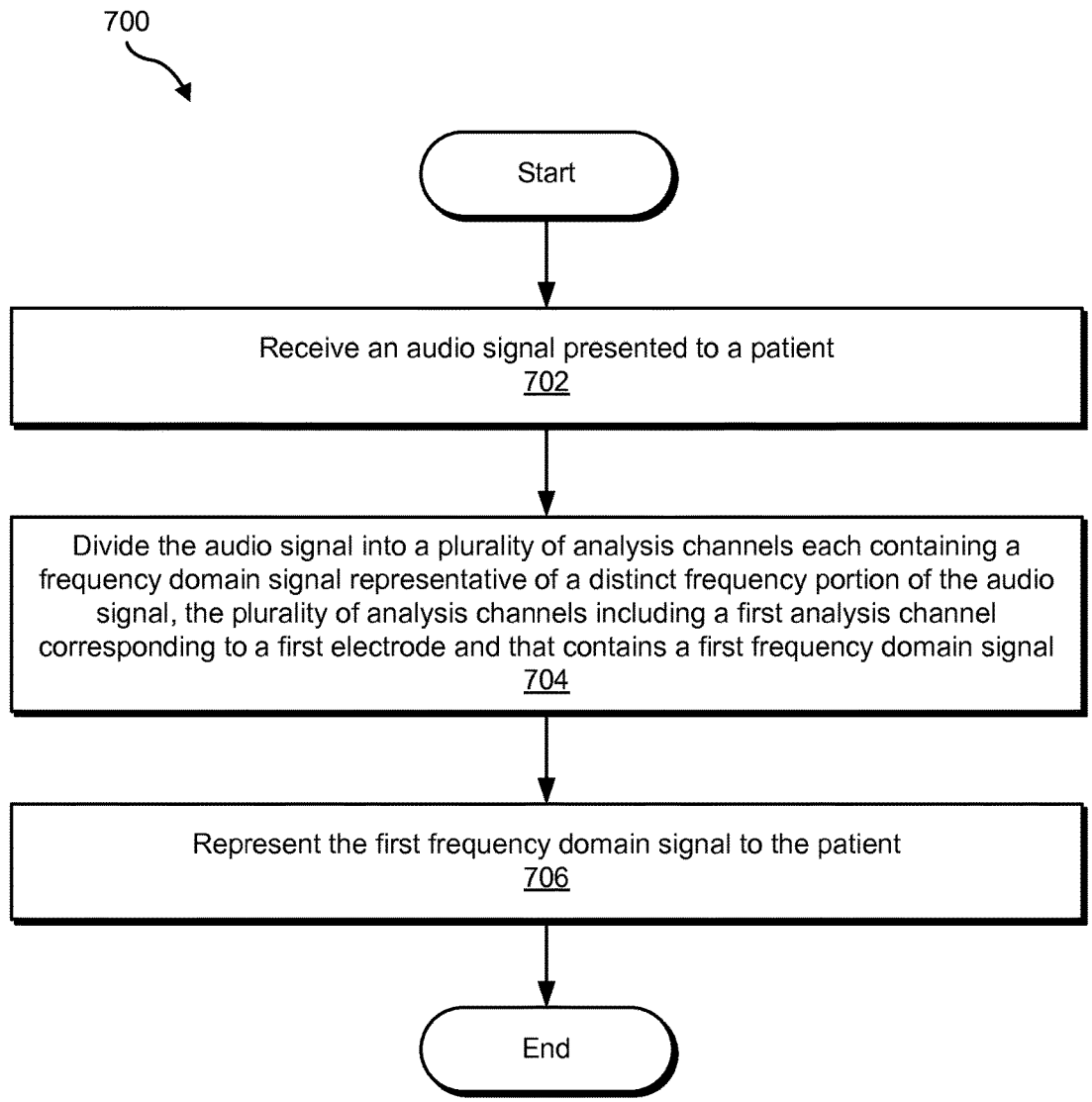
FIG. 7 illustrates an exemplary method according to principles described herein.

FIG. 7 illustrates an exemplary method 700. While FIG. 7 illustrates exemplary steps according to one embodiment, other embodiments may omit, add to, reorder, and/or modify any of the steps shown in FIG. 7. One or more of the steps shown in FIG. 7 may be performed by sound processor 104 and/or any implementation thereof.

In step 702, a sound processor, which is included in a cochlear implant system associated with a patient, receives an audio signal presented to the patient. Step 702 may be performed in any of the ways described herein.

In step 704, the sound processor divides the audio signal into a plurality of analysis channels each containing a frequency domain signal representative of a distinct frequency portion of the audio signal. The plurality of analysis channels may include a first analysis channel corresponding to a first electrode and that contains a first frequency domain signal. Step 704 may be performed in any of the ways described herein.

In step 706, the sound processor represents, after the dividing of the audio signal, the first frequency domain signal to the patient. Step 706 may be performed in any of the ways described herein. For example, the sound processor may represent the first frequency domain signal to the patient by 1) directing a cochlear implant included in the cochlear implant system to apply, during a first stimulation frame, a first monophasic stimulation pulse representative of a first temporal portion of the first frequency domain signal that corresponds to the first stimulation frame, the first monophasic stimulation pulse having a first polarity, and 2) directing the cochlear implant to apply, during a second stimulation frame that is temporally subsequent to the first stimulation frame, a second monophasic stimulation pulse representative of a second temporal portion of the first frequency domain signal that corresponds to the second stimulation frame, the second monophasic stimulation pulse configured to at least partially charge balance the first monophasic stimulation pulse and having a second polarity opposite the first polarity.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A sound processor included in a cochlear implant system associated with a patient, the sound processor comprising:
 a processing facility that
  receives an audio signal presented to the patient, and
  divides the audio signal into a plurality of analysis channels each containing a frequency domain signal representative of a distinct frequency portion of the audio signal, the plurality of analysis channels including a first analysis channel corresponding to a first electrode and that contains a first frequency domain signal; and
 a control facility communicatively coupled to the processing facility and that represents the first frequency domain signal to the patient by
  directing a cochlear implant included in the cochlear implant system to apply, during a first stimulation frame, a first monophasic stimulation pulse representative of a first temporal portion of the first frequency domain signal that corresponds to the first stimulation frame, the first monophasic stimulation pulse having a first polarity; and
  directing the cochlear implant to apply, during a second stimulation frame that is temporally subsequent to the first stimulation frame, a second monophasic stimulation pulse representative of a second temporal portion of the first frequency domain signal that corresponds to the second stimulation frame, the second monophasic stimulation pulse configured to at least partially charge balance the first monophasic stimulation pulse and having a second polarity opposite the first polarity,
 wherein:
  the first electrode is included in an array of electrodes implanted within the patient;
  the first stimulation frame corresponds to a first time period during which the first monophasic stimulation pulse is applied by the cochlear implant to the first electrode and a first set of monophasic stimulation pulses are sequentially applied by the cochlear implant to each remaining electrode included in the array of electrodes; and
  each monophasic stimulation pulse in the first stimulation frame has an opposite polarity to each directly adjacent monophasic stimulation pulse in the first stimulation frame.

2. The sound processor of claim 1, wherein the second stimulation frame corresponds to a second time period during which the second monophasic stimulation pulse is applied by the cochlear implant to the first electrode and a second set of monophasic stimulation pulses are sequentially applied by the cochlear implant to each remaining electrode included in the array of electrodes.

3. The sound processor of claim 1, wherein:
 the plurality of analysis channels further include a second analysis channel corresponding to a second electrode and that contains a second frequency domain signal, the second electrode being adjacent to the first electrode in the array of electrodes; and
 the control facility represents the second frequency domain signal to the patient by
 directing the cochlear implant to apply, after the cochlear implant applies the first monophasic stimulation pulse and during the first stimulation frame, a third monophasic stimulation pulse representative of a first temporal portion of the second frequency domain signal that corresponds to the first stimulation frame, the third monophasic stimulation pulse having the second polarity; and
 directing the cochlear implant to apply, during the second stimulation frame, a fourth monophasic stimulation pulse representative of a second temporal portion of the second frequency domain signal that corresponds to the second stimulation frame, the fourth monophasic stimulation pulse configured to at least partially charge balance the third monophasic stimulation pulse and having the first polarity.

4. The sound processor of claim 3, wherein the third monophasic stimulation pulse at least partially charge balances the first monophasic stimulation pulse.

5. The sound processor of claim 1, wherein
the control facility further
detects a difference in amplitude between the first monophasic stimulation pulse and the second monophasic stimulation pulse;
determines, based on the detected difference in amplitude, an amount of charge needed to fully charge balance the first and second monophasic stimulation pulses; and
directs the cochlear implant to apply charge balancing stimulation having the determined amount of charge during an inter-pulse interval between the first monophasic stimulation pulse and the second monophasic stimulation pulse.

6. The sound processor of claim 5, wherein, when determining the amount of charge needed to fully charge balance the first and second monophasic stimulation pulses, the control facility also takes into consideration a partial charge balancing of the first monophasic stimulation pulse that occurs as a result of a third monophasic stimulation pulse having the second polarity being applied by the cochlear implant during the first stimulation frame to an electrode adjacent to the first electrode.

7. The sound processor of claim 5, wherein the charge balancing stimulation has the first polarity if an amplitude of the second monophasic stimulation pulse is greater than an amplitude of the first monophasic stimulation pulse.

8. The sound processor of claim 5, wherein the charge balancing stimulation has the second polarity if an amplitude of the second monophasic stimulation pulse is less than an amplitude of the first monophasic stimulation pulse.

9. The sound processor of claim 5, wherein the control facility directs the cochlear implant to continuously apply the charge balancing stimulation during an entirety of the inter-pulse interval.

10. The sound processor of claim 5, wherein the charge balancing stimulation has a nominal amplitude that is not perceptible by the patient.

11. The sound processor of claim 5, wherein the inter-pulse interval has a duration substantially equal to the first stimulation frame minus a width of the first stimulation pulse.

12. The sound processor of claim 1, wherein the second stimulation frame is temporally adjacent to the first stimulation frame.

13. The sound processor of claim 1, wherein the second stimulation frame is temporally separated from the first stimulation frame by one or more intermediate stimulation frames.

14. A sound processor included in a cochlear implant system associated with a patient, the sound processor comprising:
at least one processor that
receives an audio signal presented to the patient;
divides the audio signal into a plurality of analysis channels each containing a frequency domain signal representative of a distinct frequency portion of the audio signal, the plurality of analysis channels including a first analysis channel corresponding to a first electrode and that contains a first frequency domain signal;

represents the first frequency domain signal to the patient by
directing a cochlear implant included in the cochlear implant system to apply, during a first stimulation frame, a first monophasic stimulation pulse representative of a first temporal portion of the first frequency domain signal that corresponds to the first stimulation frame, the first monophasic stimulation pulse having a first polarity; and
directing the cochlear implant to apply, during a second stimulation frame that is temporally subsequent to the first stimulation frame, a second monophasic stimulation pulse representative of a second temporal portion of the first frequency domain signal that corresponds to the second stimulation frame, the second monophasic stimulation pulse configured to at least partially charge balance the first monophasic stimulation pulse and having a second polarity opposite the first polarity; and
determines, based on an amplitude of the second monophasic stimulation pulse, an amount of charge needed to fully charge balance the first monophasic stimulation pulse; and
directs the cochlear implant to apply charge balancing stimulation having the determined amount of charge during an inter-pulse interval between the first monophasic stimulation pulse and the second monophasic stimulation pulse.

15. The sound processor of claim 14, wherein the at least one processor determines the amount of charge needed to fully charge balance the first monophasic stimulation pulse by:
detecting a difference in amplitude between the first monophasic stimulation pulse and the second monophasic stimulation pulse; and
determining, based on the detected difference in amplitude, the amount of charge needed to fully charge balance the first monophasic stimulation pulse.

16. The sound processor of claim 14, wherein the at least one processor directs the cochlear implant to continuously apply the charge balancing stimulation during an entirety of the inter-pulse interval.

17. The sound processor of claim 14, wherein the inter-pulse interval has a duration substantially equal to the first stimulation frame minus a width of the first stimulation pulse.

18. The sound processor of claim 14, wherein the second stimulation frame is temporally adjacent to the first stimulation frame.

19. A method comprising:
receiving, by a sound processor included in a cochlear implant system associated with a patient, an audio signal presented to the patient;
dividing, by the sound processor, the audio signal into a plurality of analysis channels each containing a frequency domain signal representative of a distinct frequency portion of the audio signal, the plurality of analysis channels including a first analysis channel corresponding to a first electrode and that contains a first frequency domain signal; and
representing, by the sound processor after the dividing of the audio signal, the first frequency domain signal to the patient by
directing a cochlear implant included in the cochlear implant system to apply, during a first stimulation frame, a first monophasic stimulation pulse representative of a first temporal portion of the first frequency domain signal that corresponds to the first stimulation frame, the first monophasic stimulation pulse having a first polarity; and directing the cochlear implant to apply, during a second stimulation frame that is temporally subsequent to the first stimulation frame, a second monophasic stimulation pulse representative of a second temporal portion of the first frequency domain signal that corresponds to the second stimulation frame, the second monophasic stimulation pulse configured to at least partially charge balance the first monophasic stimulation pulse and having a second polarity opposite the first polarity, wherein:

the first electrode is included in an array of electrodes implanted within the patient;

the first stimulation frame corresponds to a first time period during which the first monophasic stimulation pulse is applied by the cochlear implant to the first electrode and a first set of monophasic stimulation pulses are sequentially applied by the cochlear implant to each remaining electrode included in the array of electrodes; and each monophasic stimulation pulse in the first stimulation frame has an opposite polarity to each directly adjacent monophasic stimulation pulse in the first stimulation frame.

* * * * *